United States Patent
Meck et al.

(10) Patent No.: US 9,476,860 B2
(45) Date of Patent: Oct. 25, 2016

(54) COMPONENT FAILURE DETECTION SYSTEM

(75) Inventors: Klaus-Dieter Meck, Manchester (GB); Peter Derek Carlisle, Manchester (GB)

(73) Assignee: John Crane UK Limited, Slough (GB)

( * ) Notice: Subject to any disclaimer, the term of this patent is extended or adjusted under 35 U.S.C. 154(b) by 658 days.

(21) Appl. No.: 13/990,482

(22) PCT Filed: Dec. 2, 2011

(86) PCT No.: PCT/GB2011/001672
§ 371 (c)(1),
(2), (4) Date: Jun. 28, 2013

(87) PCT Pub. No.: WO2012/072984
PCT Pub. Date: Jun. 7, 2012

(65) Prior Publication Data
US 2013/0275056 A1    Oct. 17, 2013

(30) Foreign Application Priority Data
Dec. 2, 2010 (GB) .................................. 1020381.8

(51) Int. Cl.
*G01N 29/44* (2006.01)
*F16D 3/79* (2006.01)
(Continued)

(52) U.S. Cl.
CPC .............. *G01N 29/44* (2013.01); *F16D 3/79* (2013.01); *G01H 3/08* (2013.01); *G01M 13/028* (2013.01); *G01M 13/045* (2013.01); *F16D 2300/18* (2013.01)

(58) Field of Classification Search
CPC .. F16D 3/79; F16D 2300/18; G01M 13/028; G01M 13/045; G01H 3/08; G01N 29/44
USPC .......... 702/34, 58, 64, 73, 183, 185; 73/572; 381/94.7, 94.1, 71.1, 71.11, 71.9; 324/102
See application file for complete search history.

(56) References Cited

U.S. PATENT DOCUMENTS

| 4,493,042 A | 1/1985 | Shima et al. |
| 4,751,657 A | 6/1988 | Imam et al. |

(Continued)

FOREIGN PATENT DOCUMENTS

| DE | 102008051176 A1 | 4/2010 |
| EP | 0209862 A2 | 1/1987 |

(Continued)

OTHER PUBLICATIONS

European Patent Office, International Search Report and the Written Opinion of the International Searching Authority for International Application No. PCT/GB2011/001672 (Feb. 12, 2013).

(Continued)

*Primary Examiner* — Carol S Tsai
(74) *Attorney, Agent, or Firm* — Patterson Thuente Pedersen, P.A.

(57) ABSTRACT

An apparatus for detecting fatigue induced failure of an assembly having a single flexible element or a series of flexible elements stacked in juxtaposed engagement, for transmitting power from one component to another, the assembly having a cyclic operating speed frequency that includes at least one sensor mounted in proximity to said assembly, the sensor providing an analog signal corresponding to an airborne acoustic signal emitted by the assembly, means for amplifying the analog signal, filter means to reduce background noise from the analog signal, an analog to digital converter for converting the analog signals to a digital signal, means for sampling the digital signals in respect of the operating speed frequency of the assembly and means for analyzing the digital signals and providing an output upon the occurrence of one or more digital signal spikes in an operating cycle.

37 Claims, 7 Drawing Sheets

(51) Int. Cl.
*G01H 3/08* (2006.01)
*G01M 13/02* (2006.01)
*G01M 13/04* (2006.01)

(56) References Cited

U.S. PATENT DOCUMENTS

| | | | |
|---|---|---|---|
| 4,988,979 A | | 1/1991 | Sasaki et al. |
| 5,170,359 A | * | 12/1992 | Sax .................. G10L 25/48 324/102 |
| 5,544,080 A | * | 8/1996 | Kobayashi ......... G10K 11/1784 381/71.11 |
| 5,737,433 A | * | 4/1998 | Gardner .................. H04R 3/00 381/71.1 |
| 6,098,022 A | | 8/2000 | Sonnichsen et al. |
| 6,775,642 B2 | | 8/2004 | Remboski et al. |
| 7,640,139 B2 | * | 12/2009 | Sahara .................. G01H 1/003 702/182 |
| 2004/0112136 A1 | * | 6/2004 | Terry .................. G01M 13/028 73/572 |
| 2008/0033695 A1 | * | 2/2008 | Sahara .................. G01H 1/003 702/185 |
| 2009/0287430 A1 | * | 11/2009 | Atoji .................... G01R 31/025 702/58 |
| 2010/0101310 A1 | | 4/2010 | Perie |
| 2010/0161255 A1 | | 6/2010 | Mian et al. |

FOREIGN PATENT DOCUMENTS

| | | |
|---|---|---|
| EP | 0297729 A2 | 1/1989 |
| EP | 0317322 A2 | 5/1989 |
| EP | 0997714 A2 | 5/2000 |
| EP | 2031386 A1 | 3/2009 |
| GB | 2190198 A | 11/1987 |
| WO | WO 99/59113 | 11/1999 |
| WO | WO 99/59113 A2 | 11/1999 |

OTHER PUBLICATIONS

European Patent Office, International Search Report in International Patent Application No. PCT/GB2011/001672 (Feb. 12, 2013).

European Patent Office, Written Opinion in International Patent Application No. PCT/GB2011/001672 (Feb. 12, 2013).

* cited by examiner

COMPONENT FAILURE DETECTION SYSTEM

TECHNICAL FIELD

The present invention relates to an apparatus for detecting coupling defects of power transmission couplings during dynamic operation of rotating equipment or machinery. In particular the invention relates to the detecting of defects in power transmission couplings including a flexible assembly comprising one or more flexible elements.

BACKGROUND ART

For rotating and reciprocating equipment, non-intrusive monitoring systems are commonly used in applications where real time monitoring of the rotating and reciprocating equipment on process plants is impeded by long distances or difficulty of access. Efficient operation and maintenance of rotating and reciprocating equipment is essential to maximize production and minimize downtime. Non-intrusive monitoring systems are used to detect or predict equipment defects before catastrophic failure of the equipment occurs, which would result in loss of production capacity and possible injury of personnel.

It is desirable to detect and locate equipment defects while the equipment is in-situ so as not to interfere with the production. Removing equipment from the production for routine inspection is undesirable, as production is lost during shutdown.

Acoustic emission transducers and apparatuses to monitor specific applications and determine failure of components related to rotating equipment and machinery have been developed in the past. U.S. Pat. No. 4,493,042 to Shima et al. presents the application of acoustic monitoring to detect and judge failures of roller bearings. Other inventions were made in developing specific signal processing algorithm to determine component failure based on acoustic emission data EP2031386 A1.

Generally the acoustic emission technology used hitherto for detecting failure of components related to rotating equipment and machinery use acoustic emission sensors that are placed on a component or component surrounding structure to detect sound-waves that are transmitted through the structure (structural acoustic emission sensors).

Power transmission couplings are components that transmit torque at a speed ratio of 1:1 between the shaft ends of a driving and driven machine. They are incorporated in the drive train to compensate small misalignments between the shaft ends due to mounting tolerances and operational displacements of the shafts and minimize the bearing loads associated with the misalignment. One of the most common industrial applications of couplings is their use in refineries to connect driver and pump or driver and compressor.

In a typical power transmission coupling as illustrated in cross section in FIG. 1, a hub 102 or adapter is provided on the end of a shaft on both driven and driver equipment and a transmission unit 104 connects the hubs 102 together to transmit drive and torque from the driver equipment to the driven equipment. A flexible assembly 106 is provided as an interface between each hub 102 and transmission unit 104 to absorb angular, radial and axial misalignment between the driven and driver equipment. An example of a flexible assembly 106 is the flexible membranes found in John Crane® T Series™ and M Series™ couplings, in which the flexible assembly 106 comprises a series of flexible elements 108 as illustrated in FIG. 2. The flexible elements 108 are stacked together on juxtaposed engagement, the flexible assembly 106 being secured alternately to a hub 102 and the transmission unit 104 by an even number of bolts 110, 112, which pass through holes 114 spaced angularly about the flexible elements 108.

During each shaft revolution the flexible assembly (106) and individual flexible elements (108) are exposed to torsional stresses due to the drive torque and bending stresses due to shaft misalignment.

When operating a coupling within the specified design limits, the flexible elements achieve a theoretical infinite service life of more than $10^6$ load cycles. However, if conditions exceed the specified limit, operation beyond the misalignment limit and/or torque transmission beyond the design limit, the coupling will eventually fail due to fatigue stress cracks in the flexible elements 108 of the flexible assembly 106.

Such failure, in most cases developing over several days (weeks) from the onset of the first crack, could have costly consequences due to secondary damage to the machine or drive, production interruption and in some cases posing a severe health and safety risk.

Because each flexible assembly 106 comprises a series of individual flexible elements 108, it is difficult to detect failure of an individual flexible element 108 of flexible assembly 106. Each flexible element 108 during operation emits a different acoustic trace or signal.

Most importantly, initiation of the failure of the flexible assembly 106 starts with fretting, i.e. rubbing between individual flexible elements 108 followed by failure of a first flexible element 108 followed by failure of a second flexible element 108 and so forth. Therefore, the coupling is able to function for some time before catastrophic failure of the flexible assembly 106.

Detecting acoustic emissions emitted by a defect in the flexible element 108 of a coupling 100 using structural acoustic emission is unlikely to be successful and would not be possible with any of the existing detection technologies because a structural acoustic emission sensor cannot be placed close to the coupling's membrane unit but needs to be placed at some distance away on the machinery casing, where the sound consequently has to pass several component interfaces that eliminate the chance of detecting the signal within the noise of the surrounding machinery (bearing noise, process noise etc). For example with the coupling shown in FIG. 1, with structural acoustic emission sensors as used with detection apparatuses described in U.S. Pat. No. 4,493,042 to Shima et al., the sound would need to be transmitted from the flexible element 108 to the bolts 110, 112, from the bolts 110, 112 to the hub 102, from the hub to the machine shaft, from the shaft to a connecting bearing and from the bearing, which is a strong source of acoustic emission too, to the casing where the structural sensor is placed.

SUMMARY OF THE INVENTION

In accordance with embodiments of the present invention, it has however been found that using an acoustic emission sensor to directly detect high frequency airborne sound waves in a range between 25 kHz to 90 KHz and placing one or more of these sensors in the proximity of the coupling between 1 cm and 200 cm, sound-waves of the flexible element defects can be detected.

However, using a much lower frequency than typically used with structural acoustic emission sensors, an advanced and specific signal conditioning and detection algorithm had to be developed to differentiate a signal from the coupling membrane and other sources of sound as well as developing an algorithm that detects whether the signal constitutes a defect of one or more flexible elements 108 right up to detecting a complete failure of the flexible assembly 106.

Furthermore, many rotating and reciprocating assemblies are used on large scale process plants, and each process plant may comprise a multitude of power transmission couplings, mechanical seals, gas seals and bearings emitting different acoustic traces or resonances. Therefore, a specific fault detecting algorithm is required.

An object of embodiments of the present invention is to provide a non-intrusive component failure detection system using an acoustic method that is able to detect failure of a flexible assembly 106 of a power transmission coupling.

According to one aspect of an embodiment of the present invention an apparatus for detecting fatigue induced failure of an assembly having a single flexible element or a series of flexible elements stacked in juxtaposed engagement, for transmitting power from one component to another, the assembly having a cyclic operating speed frequency, said apparatus comprising;

at least one sensor mounted in proximity to said assembly, the sensor providing an analog signal corresponding to an airborne acoustic signal emitted by the assembly;

means for amplifying the analog signal;

filter means to reduce background noise from the analog signal;

an analog to digital converter for converting the analog signals to a digital signal;

means for sampling the digital signals in respect of the operating speed frequency of the assembly; and means for analyzing the digital signals and providing an output upon the occurrence of one or more digital signal spikes in an operating cycle.

According to another aspect of an embodiment of the present invention a method of detecting fatigue induced failure of an assembly having a single flexible element or a series of flexible elements arranged in juxtaposed engagement, for transmitting power from one component to another, the assembly having a cyclic operating speed frequency, said method comprising;

providing at least one sensor for monitoring an airborne acoustic emissions of said assembly, said sensor or sensors converting airborne acoustic signals emitted by the assembly into analog signals;

amplifying the analog signals;

filtering the analog signal to reduce background noise;

converting the analog signals to digital signals;

sampling the digital signals in respect of the operating speed frequency of the assembly; and analyzing the digital signals to determine the occurrence of one or more specific signal patterns in an operating cycle, said occurrence of one or more specific signal patterns indicating a failure of one or more of the flexible elements of the assembly.

Preferably the acoustic sensor is placed from 1 to 200 cm from the assembly, with an unobstructed path to the assembly.

According to a preferred embodiment of the invention the analog signal is filtered using an envelope demodulator which averages the peak analog signals over a time frame and replaces them with mean value analog signals.

According to a further embodiment of the present invention, the sensor for airborne acoustic emission may be connected to means for processing the acoustic signal via a node and gateway, the node being connected to the gateway wirelessly. Each node preferably comprises at least one sensor operable to measure the acoustic emission of the flexible assembly, a signal processor for processing data from said at least one sensor and a combined wireless transmitter and receiver interface; each gateway comprises a signal processor for processing data from each node and a combined wireless transmitter and receiver interface; and a computer connected to the gateway, characterized in that data from each node is transmitted to the gateway via radio frequency and said command station sends a configuration message from the gateway to each node to specify one or more analysis function to perform.

BRIEF DESCRIPTION OF THE DRAWINGS

The invention is now described by way of example only and with reference to the accompanying drawings, in which.

DETAILED DESCRIPTION

Figure 1:
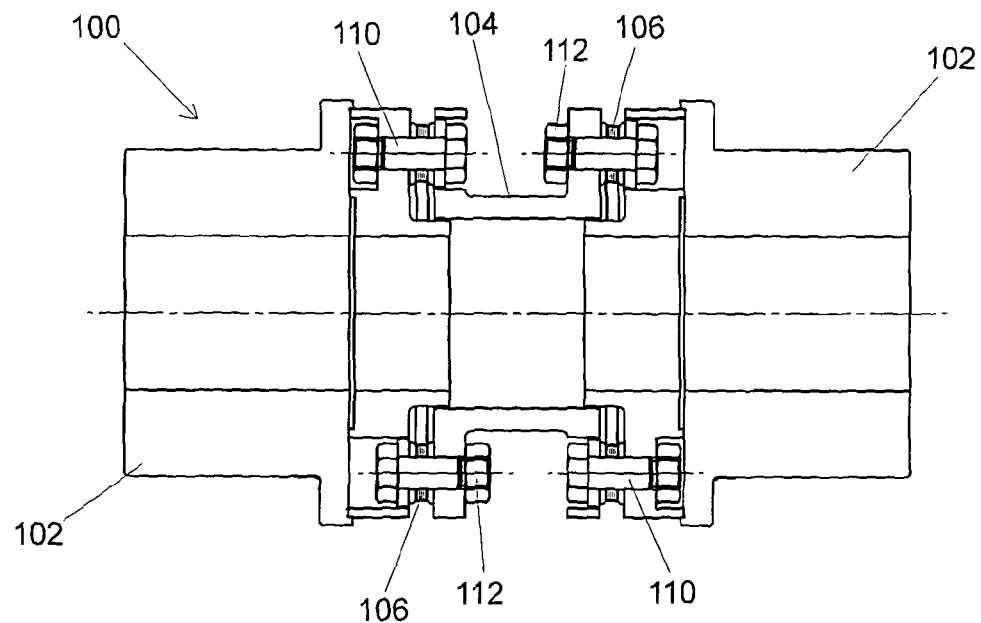
FIG. 1 illustrates a cross section of a typical membrane coupling.
Figure 2:
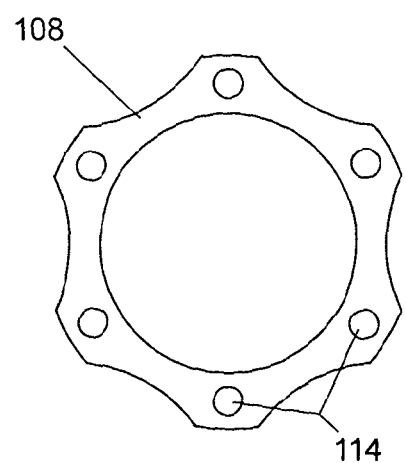
FIG. 2 illustrates a typical flexible element of the membrane coupling.
Figure 3:
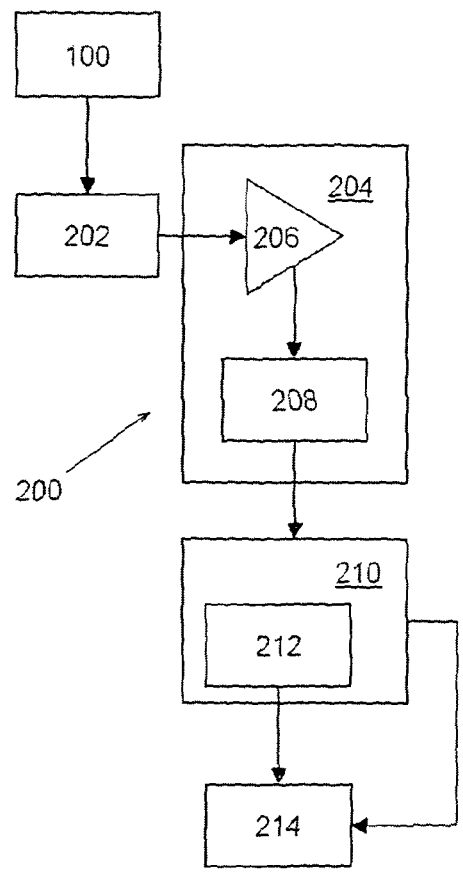
FIG. 3 illustrates an acoustic emissions detection system for determining fatigue induced failure of an assembly according to the present invention.

Referring to FIG. 3, a schematic of an acoustic emissions detection system 200 for determining fatigue induced failure of the flexible assemblies 106 of a power transmission coupling 100 according an embodiment of the present invention is shown. The acoustic emissions detection system 200 comprises an acoustic emission transducer 202 for detecting variations in acoustic signals or stress waves emitted from a stack of flexible elements 108 forming the flexible assemblies 106 of the power transmission coupling 100 shown in FIGS. 1 and 2. Such acoustic signals or stress waves are commonly generated as a result of flexing, bending, stretching and frictional stress caused by the flexible elements 108 under operation. More importantly, characteristic signals are emitted by the flexible elements 108 when a crack initiates and propagates.

The frequency bandwidth of the acoustic emission transducer 202 is selected to reduce picking up background while being sensitive enough to be able to pick up acoustic signals generated by the flexible assembly 106, by detecting the airborne acoustic signals.

The acoustic emission transducer 202 is a piezo-electric transducer designed to convert acoustic signals into an analog signals. For detecting airborne acoustic signals, the acoustic emission transducer 202 operates in a frequency range between 25 kHz to 90 kHz.

The analog signals are then sent to a control module 204. The control module 204 comprises an amplifier 206 for amplifying the analog signal and an envelope modulator 208 where the peak analog signals are averaged over a time frame and replaced by mean values. The advantages of using the envelope modulator 208 are that:

unnecessary noise is removed;
the required sampling rate for digitization is minimized; and
the computational effort for signal processing is minimized.

Figure 4:
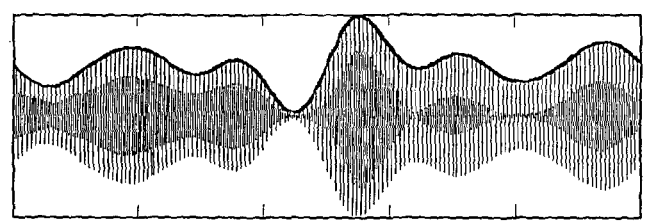
FIG. 4 illustrates enveloping of acoustic signals according to an embodiment of the present invention.

FIG. 4 illustrates the peak signals being averaged over a time frame and replaced by mean values for filtering the background noise.

The analog signals are converted into digital signal by an analog to digital converter, where the digital signals are then sent to a data acquisition module 210. The data acquisition module 210 samples the signal in discrete data sets, whereby the sampling time covers a minimum of 2 shaft revolutions. Afterwards each data set is split, whereby one set of digital signals is sent to a signal processor 212. The signal processor 212 uses a Fast Fourier Transform to calculate the frequency components of the signal -frequency domain-. The remaining signal set is left as acquired in the time domain.

Both the time domain and frequency domain of the signal are then sent to a diagnostic module 214 to determine the occurrence and frequency of signal characteristics with respect to the rotational speed of the coupling 100.

FIGS. 5 to 12 illustrate typical signals processed by the diagnostic module 214. FIGS. 5, 7, 9 and 11 illustrate the absolute digital acoustic signals acquired from the data acquisition module 210, whereby specific signal patterns are used to determine failure of each flexible element 108 as the coupling 100 rotates. FIGS. 6, 8, 10 and 12 illustrate the digital signals derived from 'using the Fast Fourier Transformation sampling process, whereby signals are analyzed in a spectrum with respect to the frequency of the coupling shaft.

Figure 5:
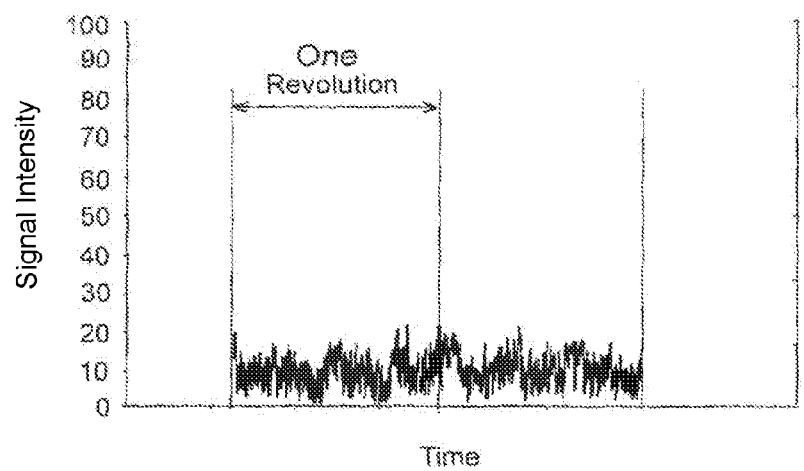
FIG. 5 illustrates absolute digitized acoustic signals of an intact coupling according to an embodiment of the present invention.
Figure 6:
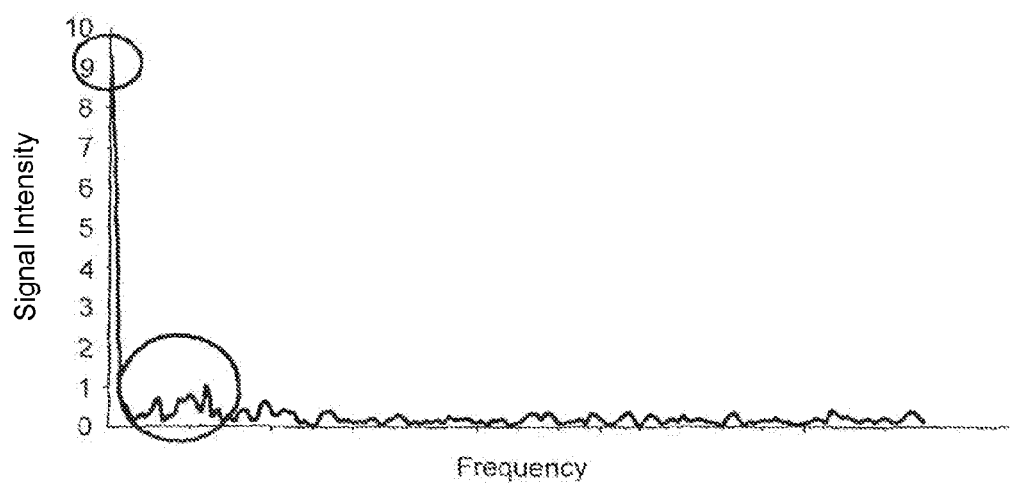
FIG. 6 illustrates the Fast Fourier Transformation Spectrum of an intact coupling according to an embodiment of the present invention.

FIGS. 5 and 6 illustrate signal intensity of a fully functional coupling without defect, wherein FIG. 5 only displays background noise. Frequencies related to the coupling shaft are absent from FIG. 6.

Figure 7:
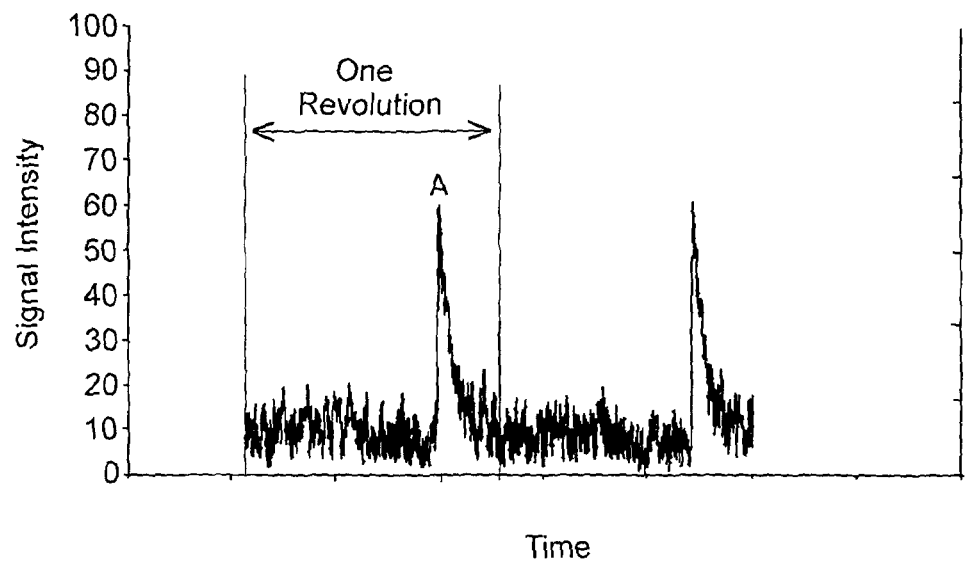
FIG. 7 illustrates acoustic signals of a coupling with one fractured flexible element according to an embodiment of the present invention.
Figure 8:
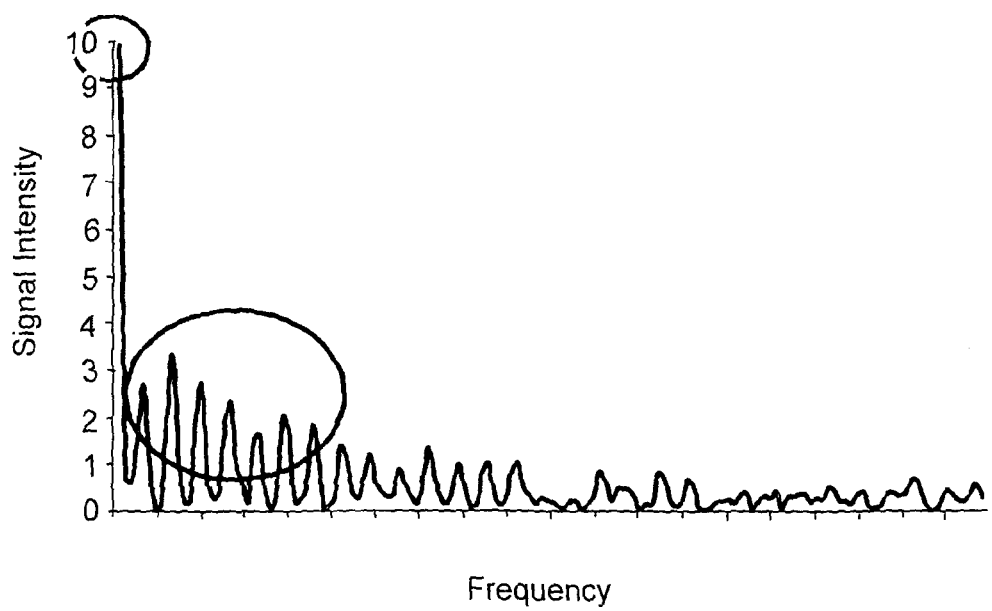
FIG. 8 illustrates the Fast Fourier Transformation Spectrum of a coupling with one fractured flexible element according to an embodiment of the present invention.

FIGS. 7 and 8 illustrate signal intensity related to a fracture of one flexible element 108 of the coupling 100. FIG. 7 displays the time domain of the sampled signal set with one dominant signal spike A and FIG. 8 displays the frequency domain of the sampled signal set that shows an increase in amplitude of the principle and harmonic frequencies related to the coupling speed.

Figure 9:
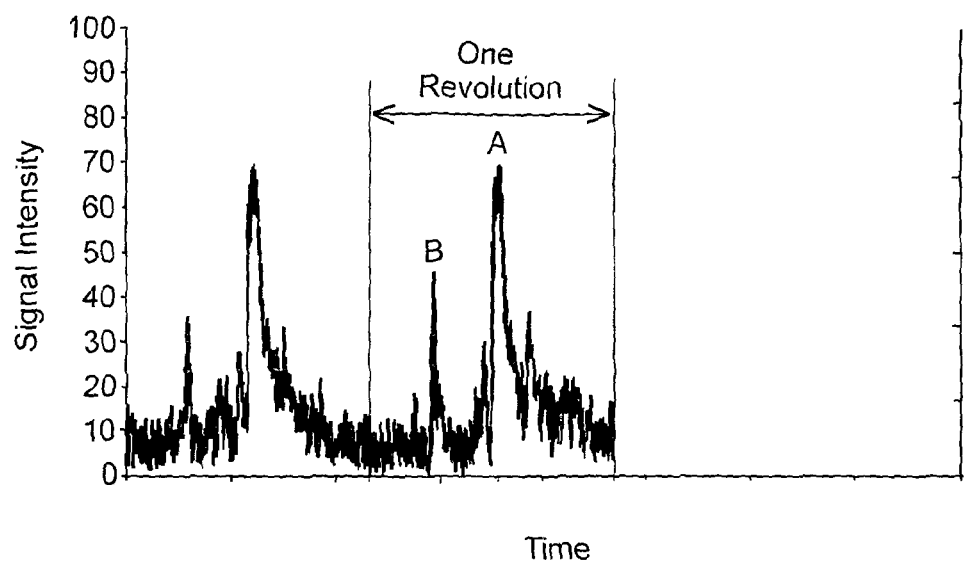
FIG. 9 illustrates acoustic signals of a coupling with two fractured flexible elements according to an embodiment of the present invention.
Figure 10:
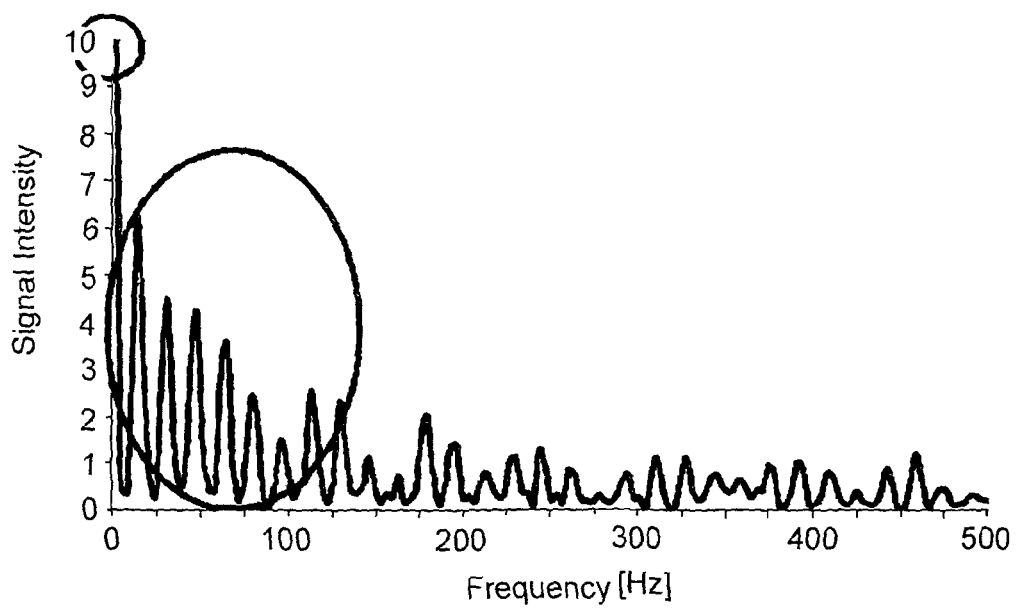
FIG. 10 illustrates the Fast Fourier Transformation Spectrum of a coupling with two fractured flexible elements according to an embodiment of the present invention.

FIGS. 9 and 10 illustrate signal intensity related to two flexible elements 108 being fractured on the coupling 100. FIG. 9 displays two signal spikes A and B, and FIG. 10 displays a further increase in the amplitude of the coupling 100 shaft frequency and a further increase in amplitude of harmonic frequencies in the frequency domain of the sampled signal set.

Figure 11:
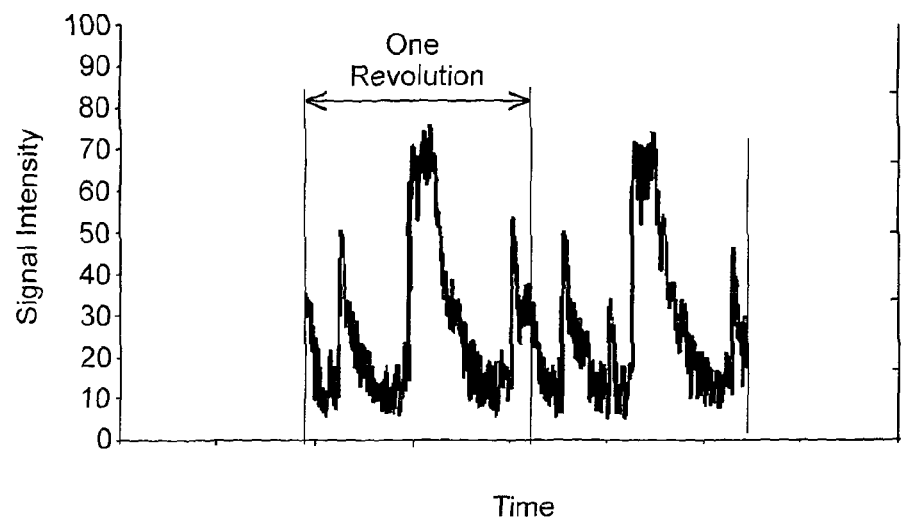
FIG. 11 illustrates acoustic signals of a coupling with three fractured flexible elements according to an embodiment of the present invention.
Figure 12:
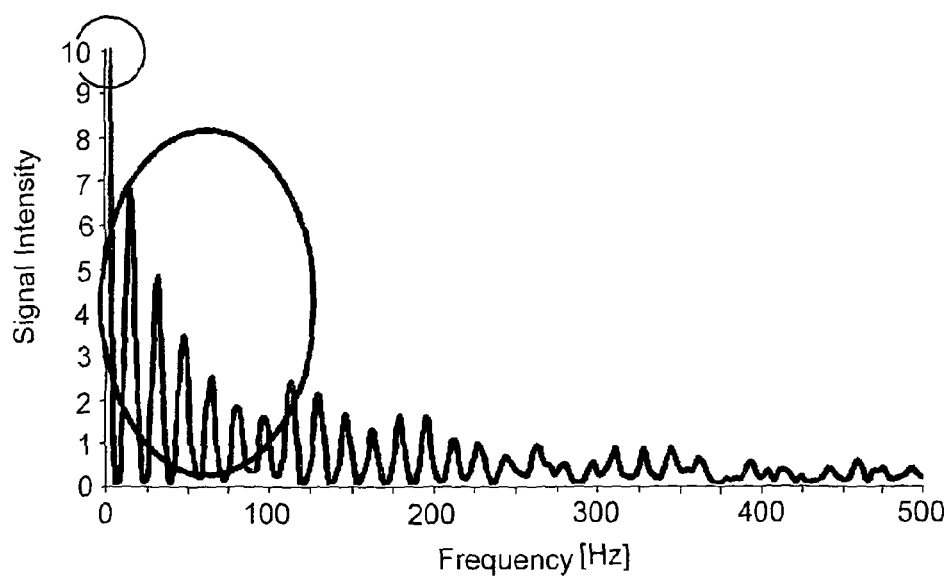
FIG. 12 illustrates the Fast Fourier Transformation Spectrum of a coupling with three fractured flexible elements according to an embodiment of the present invention.

FIGS. 11 and 12 illustrate signal intensity related to three flexible elements 108 being fractured on the coupling 100. FIG. 11 displays three signal spikes A, B and C, and FIG. 12 displays a further increase in the amplitude of the coupling 100 shaft frequency and a further increase in amplitude of harmonic frequencies in the frequency domain of the sampled signal set.

In a second embodiment, the signal processor 212 calculates high order statistical values namely Skewness and Kurtosis from the sampled signal set acquired by the data acquisition module 210 and sends the values to the diagnostic module 214 to identify coupling and non-coupling related signals and specific faults related to the flexible element 108 in a given time frame.

Figure 13:
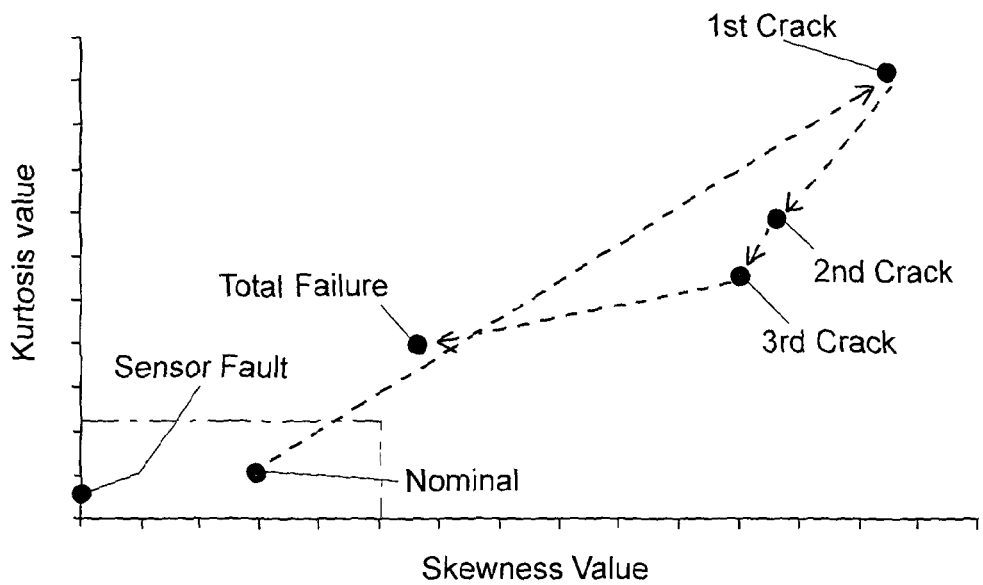
FIG. 13 illustrates the digital acoustic signals derived from a high order statistical sampling process.

FIG. 13 illustrates the signals produced by the diagnostic module 214 using the high order statistical sampling process, whereby the results from the Skewness statistical analysis is plotted against the results from the Kurtosis statistical analysis. The high order statistical sampling process has the ability to determine whether the flexible assembly 106 is in good working order or if individual flexible elements 108 have been fractured. Referring to FIG. 13, the Skewness-Kurtosis threshold provides an indication on the performance of the coupling 100.

In a third embodiment, the signal processor 212 analyzes the digital signals using the Fast Fourier Transformation process combined with the high order statistical sampling process of the second embodiment to provide an indication of the health of the flexible assembly 106. Using the following equation, the health of flexible assembly 106 can be determined:

$$\text{Coupling Health} = \frac{1}{(C3 \times C4)^2 \times e^{\frac{(FFT_{f_{shaft}} - FFT_{f_{\Sigma Z}}) + (FFT_{f_{shaft_2}} - FFT_{f_{\Sigma Z}}) + \ldots + (FFT_{f_{shaft^n}} - FFT_{f_{\Sigma Z}})}{n}}}$$

Where:

$$FFT_{f_{\Sigma Z}} = \frac{\sum_{i=1}^{Z} fi}{Z}$$

is the average FFT (Fast Fourier Transformation) for first Z frequency bands, whereby Z is an integer;
$FFT_{shaft}$ is the Fast Fourier Transformation for the first frequency of the coupling shaft;
$FFT_{shaft2}$ is the Fast Fourier Transformation for the second frequency of the coupling shaft;
$FFT_{shaftN}$ is the Fast Fourier Transformation for the $n^{th}$ frequency of the coupling shaft, whereby n is an integer and n<Z;
C3 is the Skewness value; and
C4 is the Kurtosis value.

The above equation is a typical example of mathematical statistical function used to determine coupling health. Other combinations of values in mathematical statistical function may provide similar results and may be used without departing from the scope of the invention.

As indicated above, the combined Fast Fourier Transformation and high order statistical sampling method enables the determination of the condition of the coupling for any operational speeds of the coupling 100. Therefore, such method may be applied to couplings 100 that operate on variable or fixed speeds.

Figure 14:
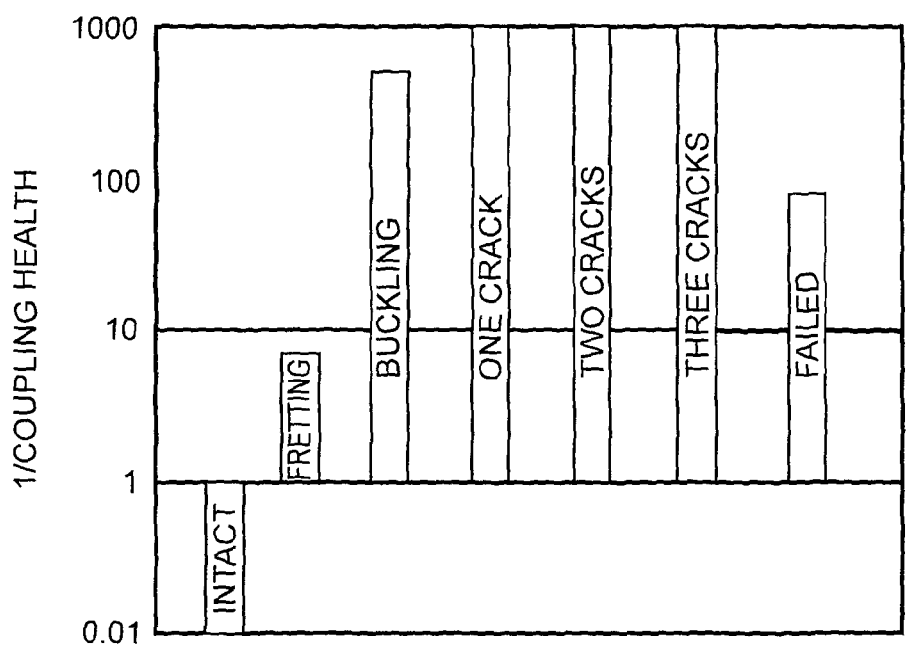
FIG. 14 illustrates the digital acoustic signals derived from combining the Fast Fourier Transformation Spectrum and the high order statistical sampling process.

Referring to FIG. 14, using the inverse of the coupling health values, the condition of the coupling 100 is illustrated in graphical format together with the threshold of the coupling health by the diagnostic module 214 for highlighting potential problems. As shown in FIG. 14, coupling condition boundaries are set to determine the health of the coupling 100. Values between 0.1 and 1 indicate that the flexible assembly 106 is in good working order, values between 1 and 10 indicate that the flexible assembly 106 has a potential problem, e.g. fretting between individual flexible elements 108, and values above 10 indicate that the coupling has failed or that cracks are present in the flexible elements 108.

In a fourth embodiment, the signal processor 212 samples the digital signals by calculating the RMS values of the digital signals over one shaft revolution. The diagnostic module 214 displays the RMS values of the signals on a graph. Although there is little to distinguish the signals of an intact coupling from the signals of a failed coupling, threshold points may be set by the user such that the diagnostic module 214 would give an indication of a potential total coupling failure.

Various modifications may be made without departing from the scope of the present invention. For example while the above embodiments have been described with reference to an envelope modulator for reducing noise, the invention is equally applicable to be used with any signal processor or signal filter that is capable of reducing background noise.

While the invention has been described with reference to an acoustic emissions detection system for determining fatigue induced failure of an assembly comprising at least one transducer, this is only an example and the invention may be used with single or multiple transducers.

In addition, the sampling processes may sample the signals continuously or intermittently over a specified time frame without departing from the scope of the invention.

The invention claimed is:

1. An apparatus for detecting fatigue induced failure of an assembly having a series of flexible elements stacked in juxtaposed engagement, for transmitting power from one component to another, the assembly having a cyclic operating speed frequency, said apparatus comprising;
    at least one sensor mounted in proximity to said assembly for receiving airborne acoustic signals emitted by the assembly, the sensor providing an analog signal corresponding to said airborne acoustic signal in the frequency range of 25 kHz to 90 kHz, emitted by the assembly;
    means for amplifying the analog signal;
    filter means to reduce background noise in the analog signal;
    an analog to digital converter for converting the analog signal to a digital signal;
    means for splitting the digital signal into two sets;
    means for sampling one of the sets of the digital signals to calculate the frequency components of the signal and provide a frequency domain signal; and
    means for analysing the frequency domain signal and the other set of digital signals and providing an output upon the occurrence of one or more specific signal patterns in an operating cycle.

2. An apparatus according to claim 1 in which the sensor is a piezo-electric transducer.

3. An apparatus according to claim 1 in which the filter means is an envelope demodulator which averages the peak analog signals over a time frame and replaces them with mean value analog signals.

4. A method of detecting fatigue induced failure of an assembly having a series of flexible elements stacked in juxtaposed engagement, for transmitting power from one component to another, the power transmission assembly having a cyclic operating speed frequency, said method comprising;
    providing a sensor for monitoring the airborne acoustic emissions of said assembly, said sensor converting acoustic signals in the frequency range of 25 kHz to 90 kHz emitted by the assembly into analog signals;
    passing the analog signal through amplifying means;
    passing the analog signal through filter means to reduce background noise;
    passing the filtered analog signal through an analog to digital converter to produce a digital signal;
    passing the digital signal through means for splitting the digital signal into two sets;
    passing one set of the digital signal through means of sampling the digital signal to calculate the frequency components of the signal and provide a frequency domain signal; and
    passing the frequency domain signal and the other set of the digital signal to means analyzing the digital signals to determine the occurrence of one or more specific signal patterns in an operating cycle, said occurrence of one or more specific signal patterns indicating a failure of one or more of the flexible elements of the assembly.

5. A method according to claim 4 in which the analog signal is filtered by passing it through an envelope demodulator which averages the peak analog signals over a time frame and replaces them with mean value analog signals.

6. A method according to claim 4 in which the digital signals are sampled using a Fast Fourier Transformation process, whereby the signals are analysed in a spectrum with respect to the operating speed frequency of the assembly, the failure of one or more of the flexible elements of the assembly producing harmonic frequencies in the Fast Fourier Transformation spectrum.

7. A method according to claim 6 in which the amplitude of the harmonic frequencies increases with the number of flexible elements to have failed.

8. A method according to claim 4 in which the digital signals are sampled using a combination of Skewness and Kurtosis statistical values to provide an indication of the failure of one or more of the flexible elements.

9. A method according to claim 4 in which the digital signals are sampled using the Fast Fourier Transformation process combined with Skewness and Kurtosis statistical values to provide an indication of the failure of one or more of the flexible elements.

10. A method according to claim 4 in which the digital signals are sampled by calculating the Root Mean Square (RMS) values of the digital signals over one cycle of the assembly.

11. An apparatus for detecting fatigue induced failure of an assembly having a series of flexible elements stacked in juxtaposed engagement, for transmitting power from one component to another, the assembly having a cyclic operating speed frequency, said apparatus comprising;
- at least one sensor mounted in proximity to said assembly for receiving airborne acoustic signals emitted by the assembly, the sensor providing an analog signal corresponding to said airborne acoustic signal emitted by the assembly;
- means for amplifying the analog signal;
- filter means to reduce background noise in the analog signal, said filter means comprising an envelope demodulator which averages the peak analog signals over a time frame and replaces them with mean value analog signals;
- an analog to digital converter for converting the analog signal to a digital signal;
- means for sampling the digital signals in respect of the operating speed frequency of the assembly; and
- means for analyzing the digital signals and providing an output upon the occurrence of one or more specific signal patterns in an operating cycle.

12. A method of detecting fatigue induced failure of an assembly having a series of flexible elements stacked in juxtaposed engagement, for transmitting power from one component to another, the power transmission assembly having a cyclic operating speed frequency, said method comprising;
- providing a sensor for monitoring the airborne acoustic emissions of said assembly, said sensor converting acoustic signals emitted by the assembly into analog signals;
- amplifying the analog signal;
- filtering the analog signal to reduce background noise by passing it through an envelope demodulator which averages the peak analog signals over a time frame and replaces them with mean value analog signals;
- converting the analog signals to digital signals;
- sampling the digital signals in respect of the operating speed frequency of the assembly; and
- analyzing the digital signals to determine the occurrence of one or more specific signal patterns in an operating cycle, said occurrence of one or more specific signal patterns indicating a failure of one or more of the flexible elements of the assembly.

13. An apparatus for detecting fatigue induced failure of an assembly for transmitting power from one component to another, the assembly having one or more flexible elements and having a cyclic operating speed frequency determined by a rotational speed of the assembly, the apparatus comprising:
- at least one sensor mounted in proximity to said assembly for receiving airborne acoustic signals emitted by the assembly, the at least one sensor providing a signal output corresponding to the airborne acoustic signals emitted by the assembly;
- a data acquisition module, configured to sample the signal output to generate a time domain representation of the signal output;
- a signal processor, configured to calculate a frequency domain representation of the signal output; and
- a diagnostic module configured to determine the occurrence of one or more signal characteristics based on the time domain representation of the signal output and the frequency domain representation of the signal output;
- whereby a condition of at least one of the one or more flexible elements is detected if at least one of the one or more signal characteristics is related to the cyclic operating speed frequency.

14. The apparatus of claim 13, wherein at least one of the signal characteristics is an increased amplitude of a specific frequency in the frequency domain representation of the signal output and wherein a signal characteristic is related to the cyclic operating speed frequency if the specific frequency is a harmonic frequency of the cyclic operating speed frequency.

15. The apparatus of claim 13, wherein the sensor is sensitive to frequencies in the range of acoustic signals emitted by the flexible elements of the assembly.

16. The apparatus of claim 13, wherein the sensor is position to sense airborne acoustic signals in the frequency range between 25 kHz and 90 kHz.

17. The apparatus of claim 13, wherein the sensor is a piezo-electric transducer.

18. The apparatus of claim 13, further comprising an envelope demodulator, configured to average the peak signal output over a time frame and replace the signal output with a mean signal output.

19. The apparatus of claim 14, wherein the signal output is an analog signal, and further comprising an analog-to-digital converter, configured to convert the analog signal to a digital signal.

20. The apparatus of claim 19, wherein the data acquisition module is further configured to split the digital signal into a first set of data and a second set of data, and wherein the signal processor generates the frequency domain representation of the signal output using the first set of data.

21. The apparatus of claim 20 wherein the signal processor calculates the frequency domain representation of the signal output using a Fast Fourier Transformation process.

22. The apparatus of claim 21 wherein the diagnostic module is further configured determine a number of flexible elements that are affected by the detected condition, whereby the determined number increases based on one or more further increases in the amplitude of at least one of the harmonic frequencies of the cyclic operating speed frequency.

23. The apparatus of claim 20, wherein the signal processor is configured to calculate a skewness value and a kurtosis value based on the second set of data.

24. The apparatus of claim 23, wherein the diagnostic module is configured to calculate a health value of the assembly based on the frequency domain representation of the signal output, the skewness value, and the kurtosis value; and whereby a condition of the assembly is detected when the health value of the assembly is indicative of a potential problem.

25. The apparatus of claim 19 wherein the signal processor is further configured sample the digital signal by calculating the Root Mean Square (RMS) values of the digital signal over one cycle of the assembly.

26. A method for detecting fatigue induced failure of an assembly for transmitting power from one component to another, the assembly having one or more flexible elements and having a cyclic operating speed frequency determined by a rotational speed of the assembly, said method comprising:
- providing at least one sensor for receiving airborne acoustic signals emitted by the assembly, the at least one sensor providing a signal output corresponding to said airborne acoustic signals emitted by the assembly;
- sampling the signal output to generate a time domain representation of the signal output;
- calculating a frequency domain representation of the signal output;

determining the occurrence of one or more signal characteristics based on the time domain representation of the signal output and the frequency domain representation of the signal output; and detecting a condition of at least one or more of the flexible elements if at least one of the one or more signal characteristics is related to the cyclic operating speed frequency.

27. The method of claim 26, wherein at least one of the signal characteristics is an increased amplitude of a specific frequency in the frequency domain representation of the signal output and wherein a signal characteristic is related to the cyclic operating speed frequency if the specific frequency is a harmonic frequency of the cyclic operating speed frequency.

28. The method of claim 26, wherein the sensor is sensitive to frequencies in the range of acoustic signals emitted by the flexible elements of the assembly.

29. The method of claim 26, further including positioning the sensor to sense airborne acoustic signals in the frequency range between 25 kHz and 90 kHz.

30. The method of claim 26, further comprising averaging the peak signal output over a time frame and replacing the signal output with a mean signal output using an envelope demodulator.

31. The method of claim 27, further comprising converting, with an analog-to-digital converter, the analog signal to a digital signal.

32. The method of claim 31, further comprising splitting the digital signal into a first set of data and a second set of data, and wherein in the frequency domain representation of the signal output is calculated using the first set of data.

33. The method of claim 32 wherein the frequency domain representation of the signal output is calculated using a Fast Fourier Transformation process.

34. The method of claim 33 further comprising determining a number of flexible elements that are affected by the detected condition, whereby the determined number increases based on one or more further increases in the amplitude of at least one of the harmonic frequencies of the cyclic operating speed frequency.

35. The method of claim 32, further comprising calculating a skewness value and a kurtosis value based on the second set of data.

36. The method of claim 35, further comprising calculating a health value of the assembly based on the frequency domain representation of the signal output, the skewness value, and the kurtosis value; and whereby a condition of the assembly is detected when the health value of the assembly is indicative of a potential problem.

37. The method of claim 31, further comprising calculating the Root Mean Square (RMS) values of the digital signal over one cycle of the assembly.

\* \* \* \* \*

UNITED STATES PATENT AND TRADEMARK OFFICE
CERTIFICATE OF CORRECTION

PATENT NO. : 9,476,860 B2  
APPLICATION NO. : 13/990482  
DATED : October 25, 2016  
INVENTOR(S) : Meck et al.

Page 1 of 1

It is certified that error appears in the above-identified patent and that said Letters Patent is hereby corrected as shown below:

In the Specification

Column 4, Line 55:
Delete "; and" and insert -- . --.

In the Claims

Claim 25, Column 10, Line 34:
Delete "configured determine" and insert -- configured to determine --.

Claim 25, Column 10, Line 51:
Delete "configured sample" and insert -- configured to sample --.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*